(12) United States Patent
Analytis et al.

(10) Patent No.: US 11,408,759 B2
(45) Date of Patent: Aug. 9, 2022

(54) PRESSURE BASED VOLUME SENSOR FOR LIQUID RECEPTACLE

(71) Applicant: Moxxly LLC, Wilmington, DE (US)

(72) Inventors: Santhi Analytis, San Francisco, CA (US); Wisit Jirattigalachote, San Francisco, CA (US); Gabrielle Guthrie, San Francisco, CA (US); Jose Luis Cordoba, San Francisco, CA (US); Jacob Kurzrock, San Francisco, CA (US); Paul Riemenschneider, San Francisco, CA (US)

(73) Assignee: Moxxly LLC, Wilmington, DE (US)

( * ) Notice: Subject to any disclaimer, the term of this patent is extended or adjusted under 35 U.S.C. 154(b) by 135 days.

(21) Appl. No.: 16/895,571

(22) Filed: Jun. 8, 2020

(65) Prior Publication Data

US 2020/0386600 A1    Dec. 10, 2020

Related U.S. Application Data

(60) Provisional application No. 62/857,955, filed on Jun. 6, 2019.

(51) Int. Cl.
| | | |
|---|---|---|
| *G01F 22/02* | (2006.01) | |
| *G01F 1/34* | (2006.01) | |
| *G01F 23/14* | (2006.01) | |
| *G01L 19/00* | (2006.01) | |
| *A61M 1/06* | (2006.01) | |
| *G01L 9/00* | (2006.01) | |

(52) U.S. Cl.
CPC ............. *G01F 22/02* (2013.01); *A61M 1/064* (2014.02); *G01F 1/34* (2013.01); *G01F 23/14* (2013.01); *G01L 9/0041* (2013.01); *G01L 19/0092* (2013.01)

(58) Field of Classification Search
CPC .... A47G 23/16; B65D 25/56; B65D 2203/04; B65D 2203/045; A61J 2200/76; G01F 22/02; G01L 9/008
See application file for complete search history.

(56) References Cited

U.S. PATENT DOCUMENTS

| | | | | |
|---|---|---|---|---|
| 2017/0326487 A1* | 11/2017 | Bratek | ................... | B01D 45/08 |
| 2018/0361040 A1* | 12/2018 | O'Toole | ................ | A61M 1/066 |
| 2021/0205510 A1* | 7/2021 | Felber | ....................... | A61J 9/00 |

\* cited by examiner

*Primary Examiner* — Herbert K Roberts
(74) *Attorney, Agent, or Firm* — Loyal IP Law, PLLC; Travis Banta

(57) ABSTRACT

Disclosed herein are various techniques and devices for detecting a level of fluid within a fluid collection receptacle. These techniques and devices may further determine a flow rate of fluid entering the fluid collection receptacle or a volume of fluid collected within the fluid collection receptacle. Sensors, including pressure sensors, may be installed in, on, or within the fluid collection receptacle to detect information about the liquid within the receptacle including fluid level, flow rate, and volume.

18 Claims, 16 Drawing Sheets

PRESSURE BASED VOLUME SENSOR FOR LIQUID RECEPTACLE

PRIORITY CLAIM

This application claims priority to and the benefit of U.S. Provisional Patent Application No. 62/857,955, filed on Jun. 6, 2019. U.S. Provisional Patent Application No. 62/857,955 is incorporated by reference in its entirety.

BACKGROUND

Technical Field

This disclosure relates generally to a liquid level sensor for detecting an amount of liquid in a liquid receptacle. In one embodiment, a liquid level sensor may obtain sensor data by detecting a level of milk in a milk bottle and using that sensor data to determine an amount of milk or volume of milk within the bottle. Sensors may be disposed within the receptacle and continuously monitor a liquid level within the receptacle and provide updated sensor data reflecting an increased liquid level.

Description of the Related Art

Receptacles for fluid storage and collection have existed since antiquity. More recently, some receptacles have been marked with graduated measurement indicators. Beakers, metal jars, measuring cups, pitchers, and a host of other fluid storage and collection receptacles have been marked with graduated measurement indicators to show how much fluid is contained within the receptacle. The graduated measurement indicators may be marked on the fluid storage and collection receptacles based on mathematical volumetric calculations to accurately reflect an amount of fluid within the fluid storage and collection receptacles. In other words, various indicators may be marked on the side of a fluid storage and collection receptacle to accurately measure a fluid level within the receptacle. For example, the receptacle may include indicators that show one ounce, two ounces, three ounces, etc., which when compared to a fluid level within the receptacle shows a person how much liquid, in fluidic measurements, is contained within the receptacle.

While these graduated indicators are helpful, their usefulness is somewhat limited. For example, in fluid collection receptacles, graduated indicators provide no indication of flow rate, e.g., how much fluid is collected per time unit. In situations where fluid collection is a slow process, a person may lose interest or be unable to monitor a flow rate due to the amount of time necessary to obtain a flow rate. Another weakness of graduated indicators is that graduated indicators are only helpful if the receptacle is in an area where it can be easily seen by a person. Thus, in applications where the fluid collection receptacle is hidden or not readily visually accessible, graduated indicators provide a person with no useful information about the volume of liquid collected within the collection receptacle.

One specific situation where graduated indicators are of limited usefulness is in nursing an infant or breast pumping. Typical breast pumps include a bottle that collects milk as it is pumped. However, in many situations, it may be inconvenient for a mother to access a bottle during pumping. For example, since a bottle is usually connected to a breast pump which is, in turn, connected to the mother's breast, it may be difficult for a mother to accurately see how much milk has been collected within the milk receptacle. Similarly, when a mother is pumping from both breasts, it may be difficult for a mother to accurately assess how much milk has been produced over a certain amount of time from each breast using nothing more than graduated indicators and a stopwatch.

Different sensor technologies have different advantages and drawbacks. For example, some types of sensors, especially in liquid receptacles associated with breast pumps, can, at times, be less accurate due to movement of the liquid receptacles during milk collection. The terms liquid receptacle and bottle may be used interchangeably. An angle of tilt of a bottle, for example, can reduce accuracy of many types of prior art sensors.

It is therefore one object of this disclosure to provide a flow rate and volume sensor system and apparatus that produces accurate results under various conditions in various environments. It is a further object of this disclosure to provide a fluid receptacle that includes one or more sensors associated with the liquid receptacle. Another object of this disclosure is to provide a sensor to sense a fluid level within a fluid receptacle and to sense a flow rate for fluid entering the receptacle. Another object of this disclosure is to provide a fluid receptacle which contains one or more sensors to accurately sense a fluid level within the fluid receptacle and sense a flow rate for milk entering the receptacle.

SUMMARY

Disclosed herein a liquid receptacle which includes a bottle and a pressure sensor element. The bottle includes a top and a bottom. The bottom of the bottle includes a hole which extends through a bottom of the bottle. The pressure sensor element may be disposed within a bottom of the bottle. The pressure sensor element may include a membrane that seals the hole which extends through a bottom of the bottle.

Further disclosed herein is a system, the system may include a flange, a manifold, a liquid receptacle, and a pressure sensor element. The manifold may be connectable to the flange and include a connector. The connector may connect to the liquid receptacle. The liquid receptacle may include a hole which extends through a bottom of the liquid receptacle. The pressure sensor element may be disposed in a bottom of a liquid receptacle and include a membrane that seals the hole which extends through a bottom of the liquid receptacle.

BRIEF DESCRIPTION OF THE DRAWINGS

The accompanying drawings illustrate one or more embodiments of a fluid collection receptacle which includes one or more sensors for accurately assessing both a flow rate and amount of milk contained within the fluid collection receptacle.

DETAILED DESCRIPTION OF PREFERRED EMBODIMENTS

In the following description, for purposes of explanation and not limitation, specific techniques and embodiments are set forth, such as particular techniques and configurations, in order to provide a thorough understanding of the device disclosed herein. While the techniques and embodiments will primarily be described in context with the accompanying drawings, those skilled in the art will further appreciate that the techniques and embodiments may also be practiced in other similar devices.

Reference will now be made in detail to the exemplary embodiments, examples of which are illustrated in the accompanying drawings. Wherever possible, the same reference numbers are used throughout the drawings to refer to the same or like parts. It is further noted that elements disclosed with respect to particular embodiments are not restricted to only those embodiments in which they are described. For example, an element described in reference to one embodiment or figure, may be alternatively included in another embodiment or figure regardless of whether or not those elements are shown or described in another embodiment or figure. In other words, elements in the figures may be interchangeable between various embodiments disclosed herein, whether shown or not.

Figure 1:
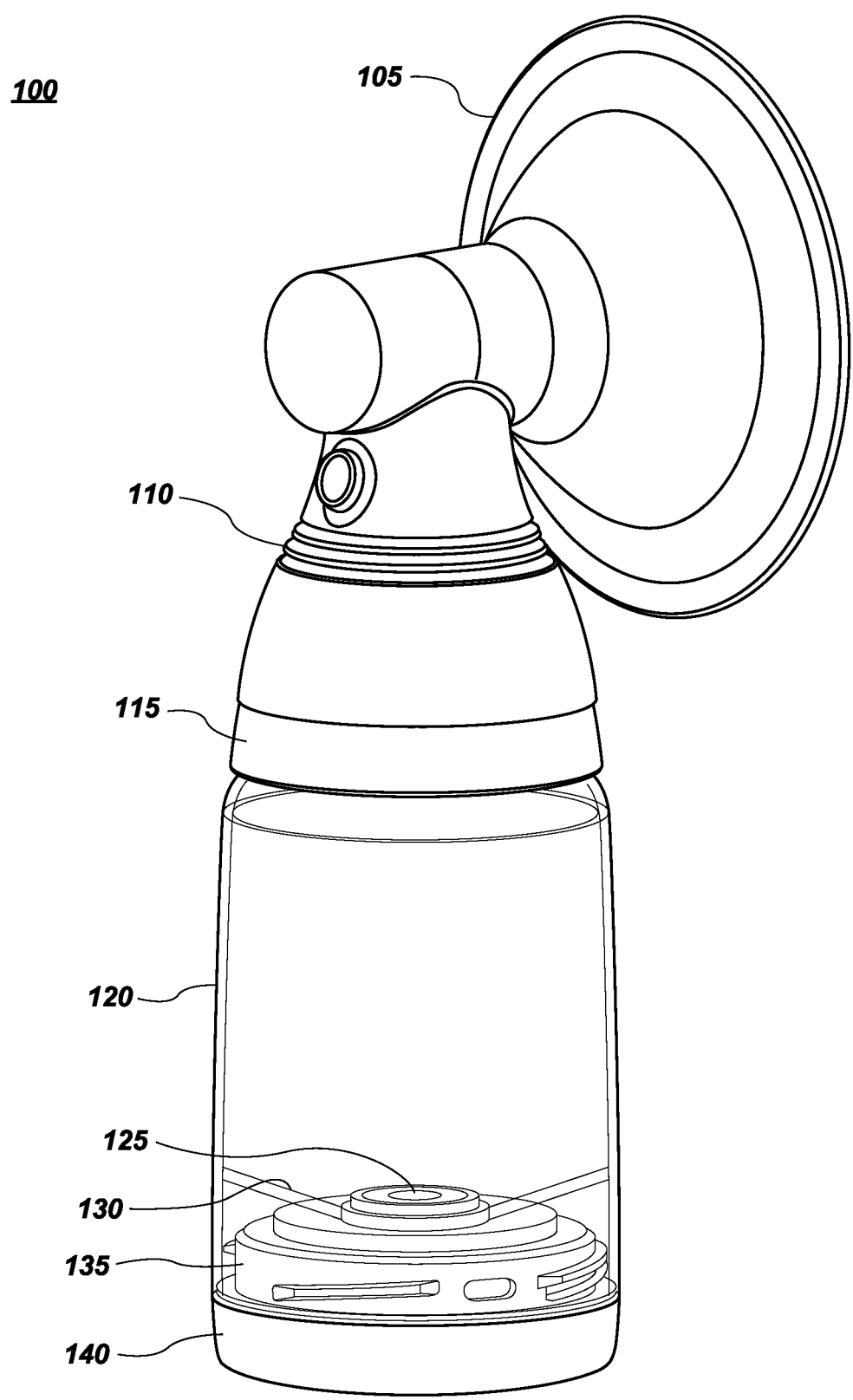
FIG. 1 illustrates breast pump including a fluid collection receptacle and one or more sensors.

FIG. 1 illustrates a breast pump 100 including a fluid collection receptacle 120 and one or more sensors 135. Breast pump 100 may include a flange 105 which may be removable from manifold 110. Manifold 110 may house a number of elements, which are not shown in FIG. 1, including computer hardware, one or more processors, various types of memory (static, dynamic, flash, etc.), receivers, transmitters, antennas, various sensors, a vacuum pump, and other elements that make breast pump 100 capable of interacting with, for example, a mobile device, such as a mobile phone. A vacuum pump, not shown, may also be a component that is external to breast pump 100 and may connect to breast pump 100. Manifold 110 may further include a connector 115 for attaching liquid receptacle 120 to manifold 110. Connector 115 may use any appropriate mechanism, including male and female threads, for connecting manifold 110 to liquid receptacle 120.

Liquid receptacle 120 may also be implemented as a bottle and be made of any suitable material including various types of plastics. Liquid receptacle 120 may include a bottom 130 which includes a hole in which a membrane 125 may be positioned. Membrane 125 may be used to sense an amount of pressure within liquid receptacle 120 that corresponds to an amount of fluid within liquid receptacle 120. As will be discussed below, the amount of pressure exerted on membrane 125, which is a non-permeable membrane, may be transferred into a pressure sensor component, not shown, housed in an enclosure 135 for detecting an amount of fluid within receptacle 120. Pressure sensor enclosure 135 may further contain electrical components, such as a pressure sensor, a processor, batteries, and other electrical components suitable to operate pressure sensor component 135, such as those described above with respect to manifold 110. Liquid receptacle 120 may extend past a bottom 130 of liquid receptacle 120 to provide a threaded connection to pressure sensor component 135. Pressure sensor enclosure 135 may further include corresponding threads to mate with liquid receptacle 120. Breast pump 100 may further include a base 140 which may be connected to pressure sensor component housed within 135, or which may be a separate individual element. Base 140 attaches to breast pump 100 and allows breast pump 100 to stand upright.

Figure 2:
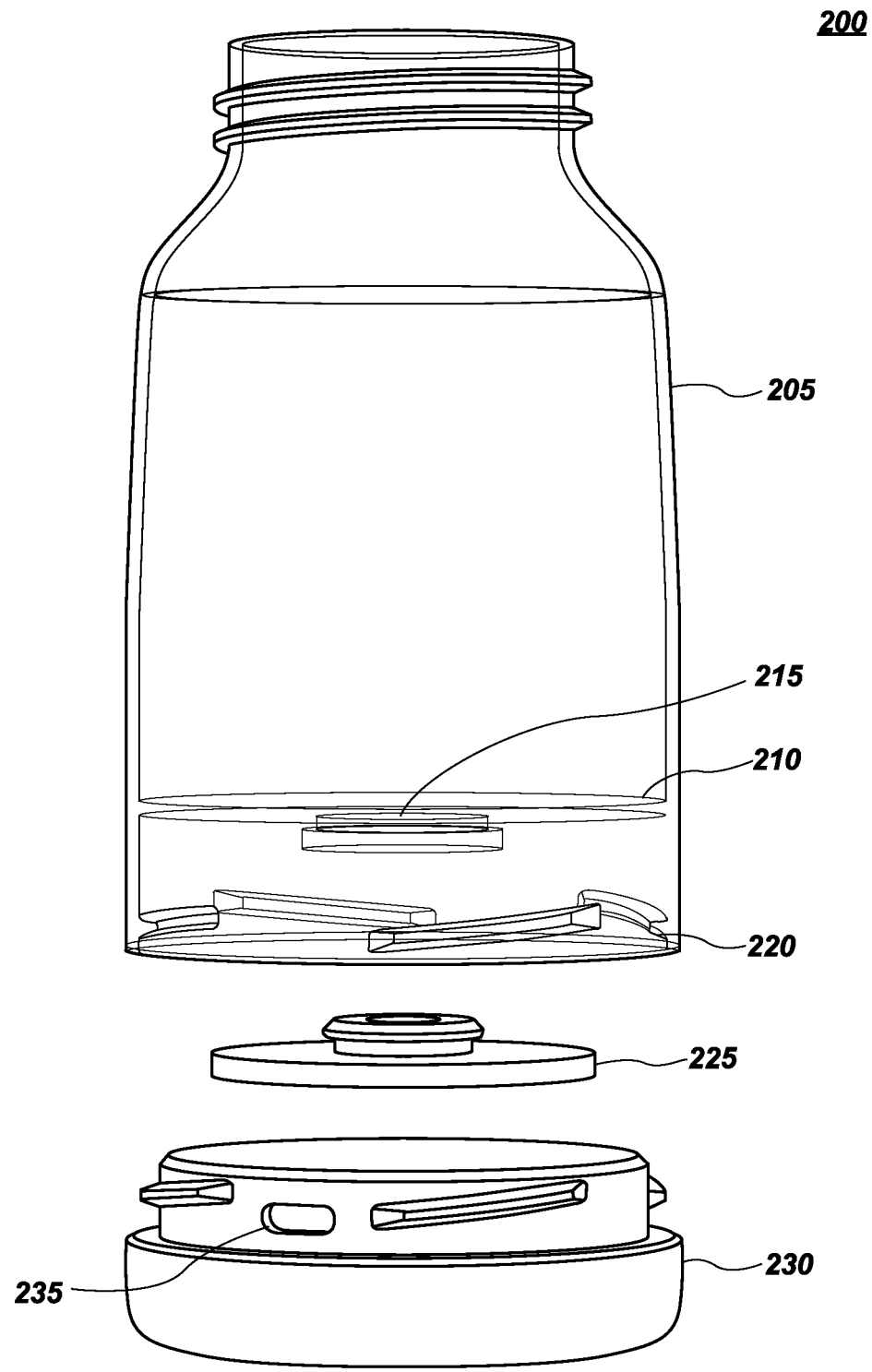
FIG. 2 illustrates an exploded view of the fluid collection receptacle including one or more sensors.

FIG. 2 illustrates an exploded view of the fluid collection receptacle 200, which is similar in implementation and description to fluid collection receptacle 120, shown in FIG. 1, and including one or more sensors within pressure sensor component 230, which are similar in implementation and description to pressure sensor component 135, shown in FIG. 1. Fluid collection receptacle 200 includes a bottle 205. Bottle 205 may include a bottom 210 which may be sloped, or funneled, downwards towards a hole 215 at the lowest point of the slope of bottom 210. In this manner, liquid contained within bottle 205 may be directed downwards by gravity towards hole 215. Bottle 205 may extend past bottom 210 and provide a threaded connection to pressure sensor component 230. Fluid collection receptacle 200 may further include a membrane 225, which is a non-permeable membrane. Membrane 225 may be installed on a top of pressure sensor component 230 and such that membrane 225 is installed on a bottom portion of hole 215. Membrane 225 may seal to bottom 210 to prevent leakage of a liquid from bottle 205 through hole 215.

Pressure sensor component 230 may include a pressure sensor connected to a tortuous path, a path through which air may be compressed by pressure created by liquid within bottle 205. The pressure sensor, which will be discussed in more detail below, may detect an increase in pressure caused by liquid within bottle 205 and communicate data representative of the pressure and pressure increase to a processor contained within pressure sensor component 230. Pressure sensor component 230 may also include a battery for providing power to pressure sensor component 230. The battery may be connected to a power port 235, which may be a USB, mini-usb, micro-usb, or any other similar connection known in the art. Alternatively, charging may accomplished wirelessly. Power port 235 may be an access point where pressure sensor component 230 may receive and transmit both power and information, such as pressure information, liquid volume information, or any other information generated within breast pump 100 and liquid receptacle 200.

Figure 3:
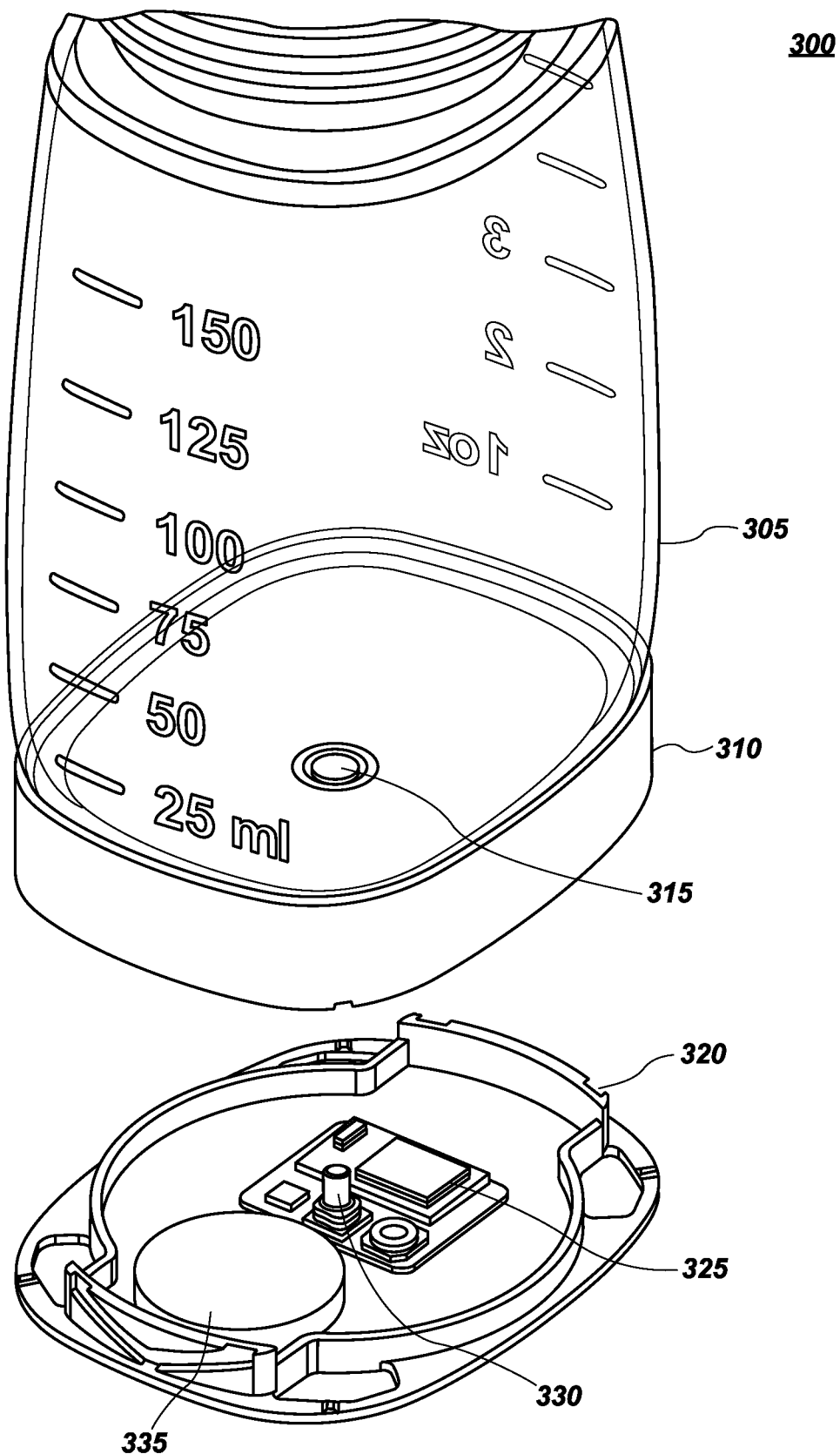
FIG. 3 illustrates a perspective exploded view of the fluid collection receptacle including one or more sensors.

FIG. 3 illustrates a perspective exploded view of the fluid collection receptacle 300 including one or more sensors. Fluid collection receptacle 300 may be implemented in a manner similar to fluid collection receptacle 200 shown in FIG. 2 and fluid collection receptacle 100, shown in FIG. 1. Fluid collection receptacle 300 may include a bottle 305 which includes a bottom 310 which slopes down, or funnels, to a hole 315 in bottom 310. A membrane (such as membrane 225, shown in FIG. 2 but not visible in FIG. 3 due to perspective) may be disposed in hole 315 which seals to bottom 310 and prevents liquid within bottle 305 from leaking through hole 315.

FIG. 3 includes a pressure sensor component 320 which is similar in implementation and description to pressure sensor component 135, shown in FIG. 1 and pressure sensor component 230, shown in FIG. 2, may include a processor 325, a plurality of sensors 330, and a battery 335. Sensors 330 may be a pressure sensor, an accelerometer to detect a tilt angle of bottle 305, and a temperature sensor to detect a temperature of bottle 305 or surrounding area. Sensors 330 may communicate data to processor 325 such that processor 325 may determine an amount of liquid within bottle 305. For example, processor 325 may receive information representative of a condition in which bottle 305 is disposed at an angle at a certain pressure and, based on this information, calculate a volume of liquid within bottle 305. Similarly, processor 325 may receive information representative of a condition in which bottle 305 is at a particular temperature and has a certain pressure and, based on this information, calculate a volume of liquid within bottle 305. Likewise, processor 325 may receive information representative of a condition in which bottle 305 is disposed at a particular angle, has a certain temperature, and a certain pressure and, based on this information, calculate a volume of liquid within bottle 305. It is also possible that processor 325 may calculate a volume of liquid within bottle 305 based on pressure data from the pressure sensor of sensors 330. Processor 325 may further determine a flow rate of fluid entering the fluid collection based on pressure data from the pressure sensor.

Figure 4:
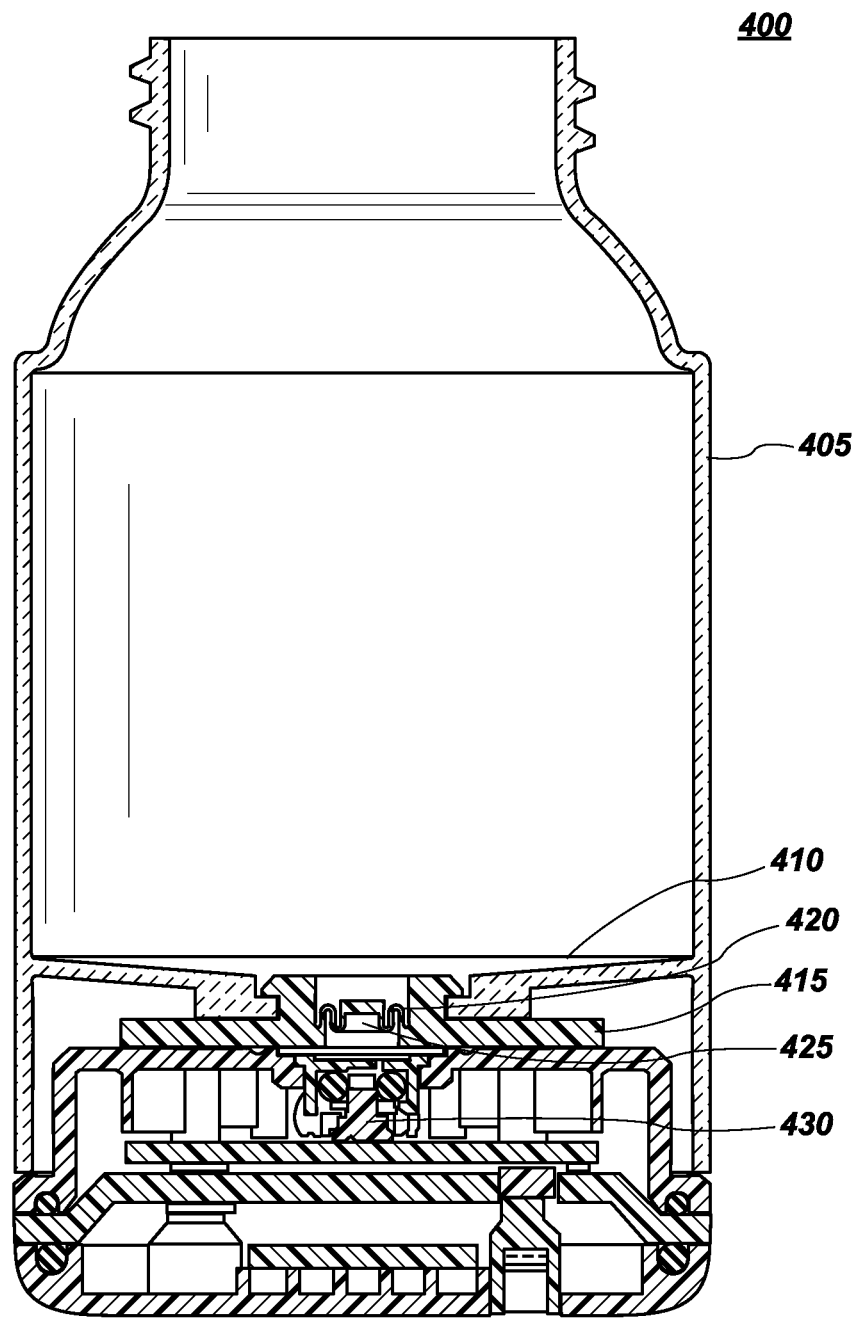
FIG. 4 illustrates a cross sectional view of one embodiment of a fluid collection receptacle including one or more sensors.

FIG. 4 illustrates a cross sectional view of one embodiment of a fluid collection receptacle 400 including one or more sensors. Fluid collection receptacle 400 is implemented as a closed system, which means that a membrane, such as those previously discussed, form a barrier between liquid within bottle 405 and an air chamber above the sensor, as will be discussed below. It is also possible to implement a direct contact system, which means that the membrane has a hole in the center so there is no physical barrier between liquid within bottle 405 and an air chamber above the sensor, as will be discussed relative to other embodiments. It should also be noted that a membrane is optional in both closed systems and direct contact systems. For example, a sensor enclosure or a bottom of a bottle with a co-molded gasket may provide sealing and flexible features of the membrane in lieu of the membrane.

Bottle 405 may be similar in implementation and description to liquid collection receptacle 120 shown in FIG. 1, bottle 205 shown in FIG. 2, and bottle 305 shown in FIG. 3. Bottle 405 provides additional interior detail of a closed system for a pressure based sensor. Bottle 405 includes a bottom 410 which slopes downwards, or funnels, to a hole in a central portion of bottom 410 and a membrane 420 which covers the hole in bottom 410. Membrane 420 includes a membrane element 415 which is flexible plastic material and seals an air chamber 425 from bottom 410 and liquid contained therein. Membrane element 415 may be constructed from flexible plastic material and secure an IPX 70 rated membrane to bottom 410 of body 405. Or, alternatively, membrane element 415 may be provided as a tube which allows air in air chamber 425 to be unconstrained and expand freely. Membrane element 415 secures membrane 410 in place while also providing a seal to a bottom 410 of bottle 405.

Pressure sensor 430, in this embodiment, may be implemented within air chamber 425 such that differences in pressure within air chamber as a result of liquid pushing on membrane 420 may be detected by pressure sensor 430. Other elements, which are not shown in FIG. 4 such as a processor, temperature sensors, accelerometers, and batteries, may be used to determine, based on data received from any of these sensors, a volume of liquid within bottle 405.

Without closed membrane 415, air in air chamber 425 may come into contact with liquid in bottle 405. In this embodiment, a temperature sensor detects that the air in air chamber 425 and liquid in bottle 405 have the same temperature and pressure shifts due to liquid temperature are negligible to determining a volume of liquid within bottle 405. As liquid fills bottle 405, air in air chamber 425 may be trapped within air chamber 425 and become increasingly pressurized as the volume of liquid increases within bottle 405. Pressure sensor 430 may detect these pressure increases and provide pressure data to a processor to determine a volume of liquid within bottle 405.

Figure 5:
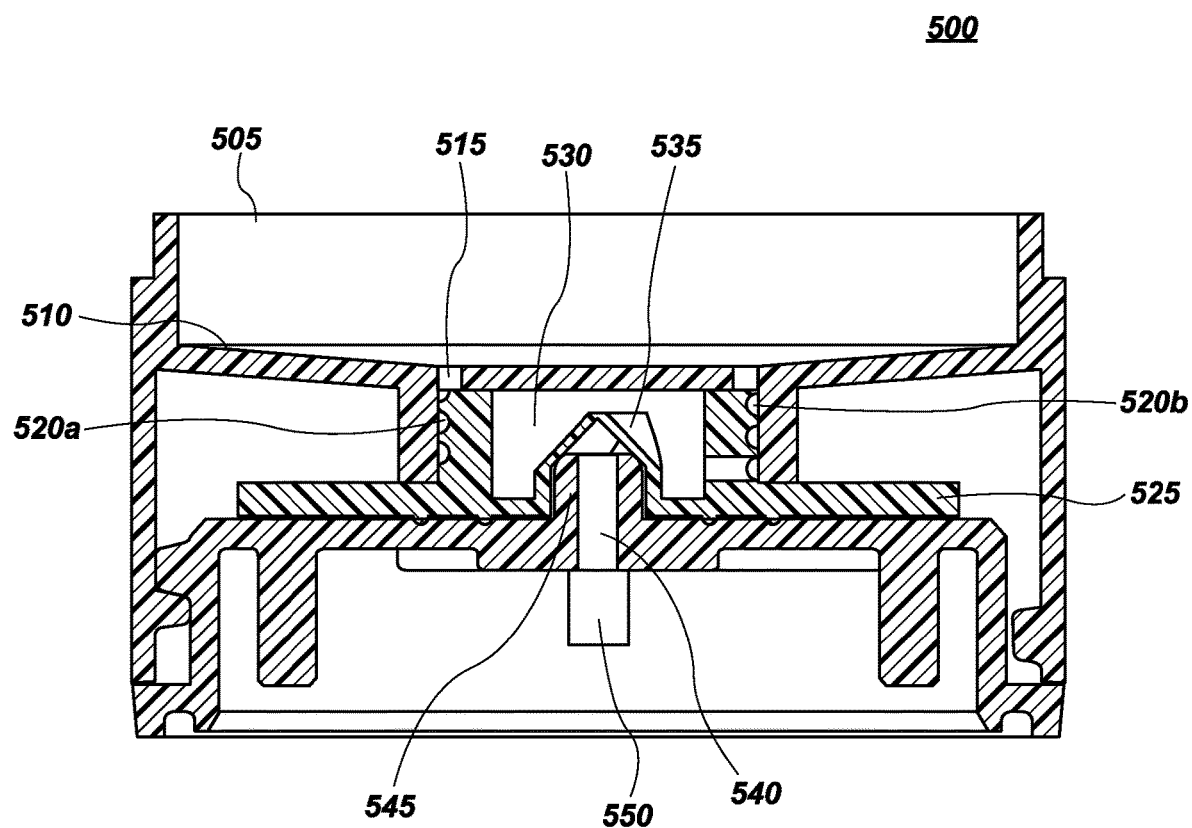
FIG. 5 illustrates another embodiment of a fluid collection receptacle including one or more sensors.

FIG. 5 illustrates another embodiment of a fluid collection receptacle 500 including one or more sensors. For example, fluid collection receptacle 500 includes a bottle 505 which includes a bottom 510 which is sloped downwards, in a funnel shape, to a hole 515 in bottom 510. Hole 515 leads to a spiraling tortuous path 520. As fluid enters tortuous path 520a, fluid pushes on air within air chamber 530 via an opening 520b at an end of tortuous path 520a. Since air chamber 530 is sealed by membrane element 525, pressure within air chamber 530 increases as more and more liquid is contained within bottle 505.

Membrane 525 includes a valve 535 which prevents liquid from pushing into air chamber 530 and into air tube 540. A mechanical activator 545 opens the valve during insertion, connecting the air chamber under the liquid receptacle to the air tube. However, valve 535 allows air to pass through valve 535 and down into pressure sensor 550. Pressure sensor 550 may detect these pressure changes and communicate pressure information to a processor for determining an amount of volume contained within bottle 505. Batteries, temperature sensors, and accelerometer sensors may also be included but are not shown in FIG. 5.

Figure 6A:
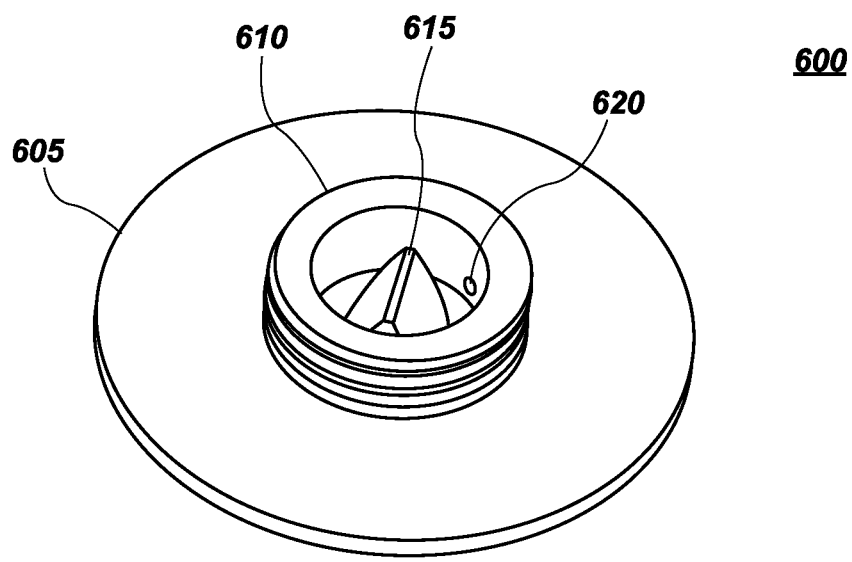
FIG. 6A illustrates a top perspective view of an embodiment of a membrane associated with the fluid collection receptacle.

FIG. 6A illustrates a top perspective view of an embodiment of a membrane 600 (such as 525 in FIG. 5) associated with a fluid collection receptacle, such as fluid collection receptacles discussed herein. Membrane 600 may include a membrane element 605 which is constructed from a flexible plastic. Membrane element 605 may include a cylindrical protrusion 610 about an external portion of which provides a spiraling tortuous path that provides access through a hole 620 into an air chamber within cylindrical protrusion 610. Within cylindrical protrusion 610, a valve 615 may be installed which prevents liquid from passing through and into a pressure sensor, as described above. Membrane element 605 may be used to close a hole in a bottom of a bottle and also provides advantages in cleanability when membrane element 605 is separable from the bottle and the pressure sensor component (as shown in FIG. 2). Membrane element 605 may also be implemented through a simple manufacturing process because membrane element 605 may be separated from other rigid elements in the breast pump.

Figure 6B:
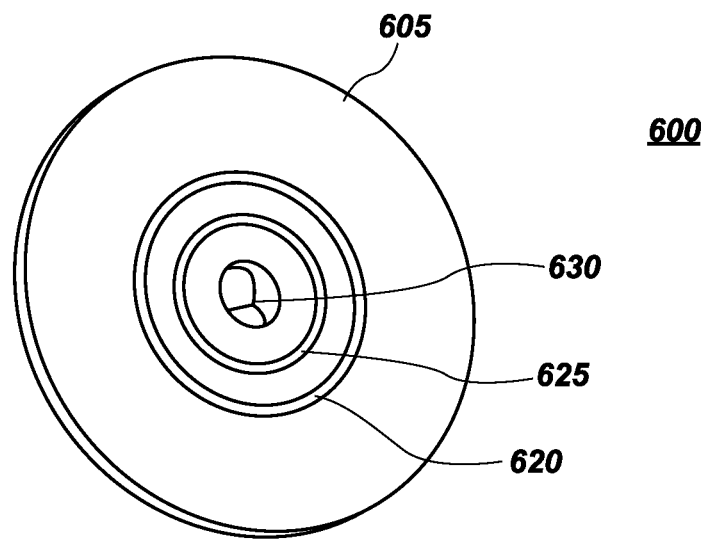
FIG. 6B illustrates a bottom perspective view of an embodiment of a membrane associated with the fluid collection receptacle.

FIG. 6B illustrates a bottom perspective view of an embodiment of a membrane 600 associated with the fluid collection receptacle. Membrane 600 is shown in FIG. 6B as an underside of membrane 600 shown in FIG. 6A. Membrane 600 includes a membrane element 605. Membrane element 605 may be constructed from a flexible plastic. Installed in the flexible plastic are a one or more gaskets such as gasket 620 and gasket 625. Gasket 620 and gasket 625 seal membrane 600 to, for example, a pressure sensor component, such as pressure sensor component 230, shown in FIG. 2. Membrane element 605 further includes a view of valve 630 which prevents liquid from passing through the valve and into a pressure sensor, as described above. Valve 630 allows only air to pass into an air tube, such as air tube 540, shown in FIG. 5, as a bottle receives more and more fluid.

Figure 7A:
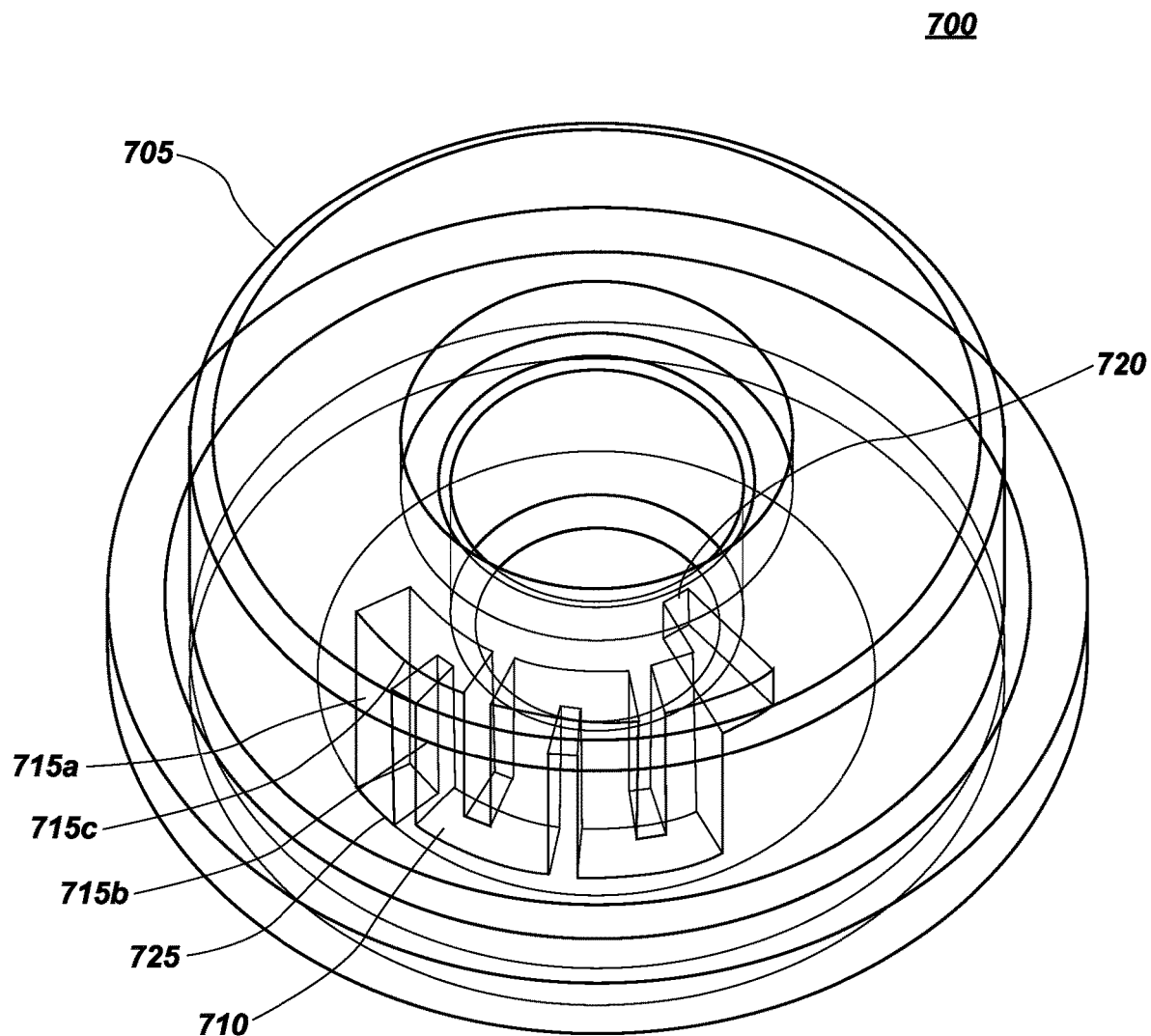
FIG. 7A illustrates an embodiment of a tortuous path within a fluid collection receptacle including one or more sensors.

FIG. 7A illustrates an embodiment of a tortuous path 720 within a fluid collection receptacle 700 including one or more sensors in a pressure sensor component 705. Pressure sensor component 705 may be similar in implementation and description to other pressure sensor components disclosed herein. Further, pressure sensor component 705 as shown in FIGS. 7A-7D is shown only to highlight one embodiment of a tortuous path 720 that may be used in connection with other disclosure presented herein. Tortuous path 720 is intended to be a series of switchbacks or snake-like set of turns to force liquid to fight gravity (e.g., with upward turns or with 180 degree turns). The tortuous path may be implemented in a bottle, in a membrane, or between an interface of the bottle and membrane.

Tortuous path 720 shown in FIG. 7A may be a partial right angle snake path. For example, tortuous path 720 may include one or more lower horizontal portions 710 which are connected to a vertical element 715a/715b by right angles. Tortuous path 720 may further include one or more upper horizontal portions 715c which connect to vertical elements 715a/715b at right angles. Tortuous path 720 may be implemented with a plurality of lower horizontal portions 710, a plurality of upper horizontal portions 715c, and a plurality of vertical portions 715a/715b. Liquid received into tortuous path 720 may have a tortuous route to pass through, requiring increasingly more and more pressure to compress air within tortuous path 720. Tortuous path 720 may include an output 725.

Figure 7B:
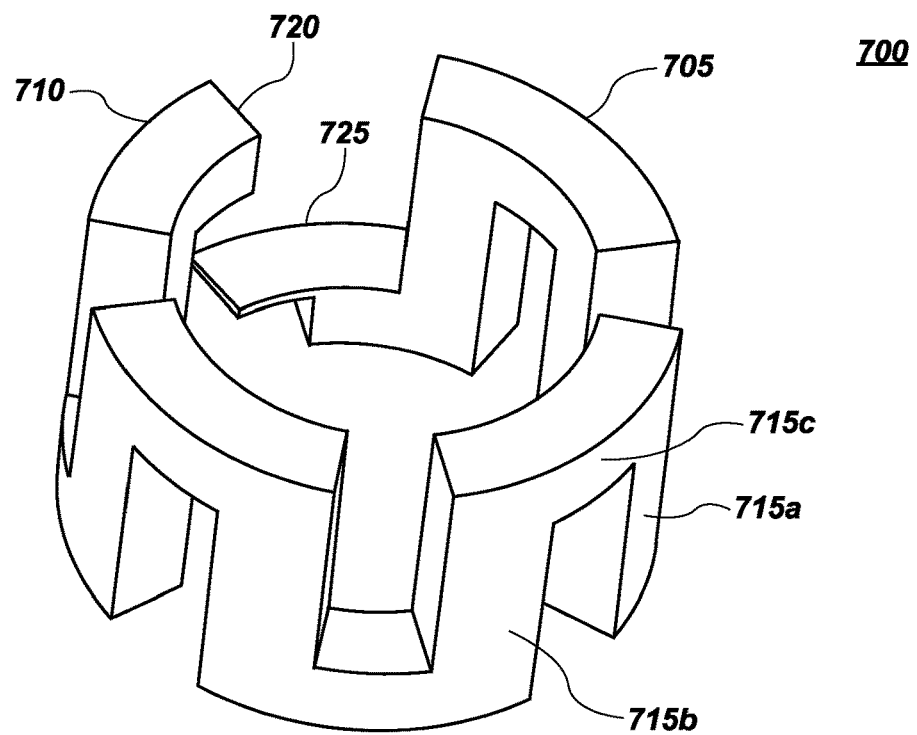
FIG. 7B illustrates an alternative embodiment of a tortuous path within a fluid collection receptacle including one or more sensors.

FIG. 7B illustrates an alternative embodiment of a tortuous path 720 within a fluid collection receptacle 700 including one or more sensors in a pressure sensor component 705. Tortuous path 720 may be termed a full right angle snake path, essentially completing a full circle of the partial right angle snake path illustrated in FIG. 7B. For example, tortuous path 720 may include one or more lower horizontal portions 710 which are connected to a vertical element 715a/715b by right angles. Tortuous path 720 may further include one or more upper horizontal portions 715c which connect to vertical elements 715a/715b at right angles. Tortuous path 720 may be implemented with a plurality of lower horizontal portions 710, a plurality of upper horizontal portions 715c, and a plurality of vertical portions 715a/715b. Liquid received into tortuous path 720 may have a tortuous route to pass through, requiring increasingly more and more pressure to compress air within tortuous path 720. Tortuous path 720 may include an output 725. As shown in FIG. 7B, a full 360 degree circle is created for tortuous path 720.

Figure 7C:
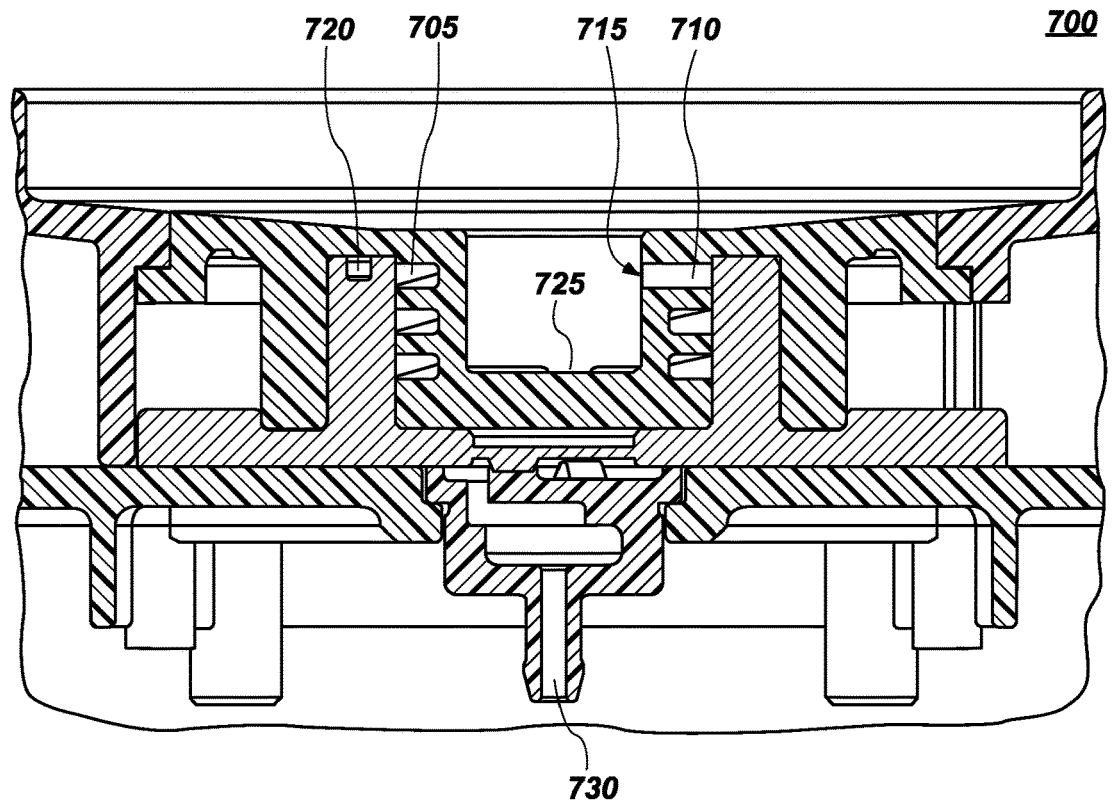
FIG. 7C illustrates an alternative embodiment of a tortuous path within a fluid collection receptacle including one or more sensors.

FIG. 7C illustrates an alternative embodiment of a tortuous path 720 within a fluid collection receptacle 700 including one or more sensors in a pressure sensor component 705. FIG. 7C illustrates a dual spiral tortuous path 720 that spirals down and then up. For example, as liquid enters tortuous path 720, the liquid is forced down through spiral 710 (shown in cross section) and back up through spiral 710 into an output 715 into air chamber 725. As air pressure builds up in air pressure chamber 725, air is compressed within tube 730 and detected by a pressure sensor.

Figure 7D:
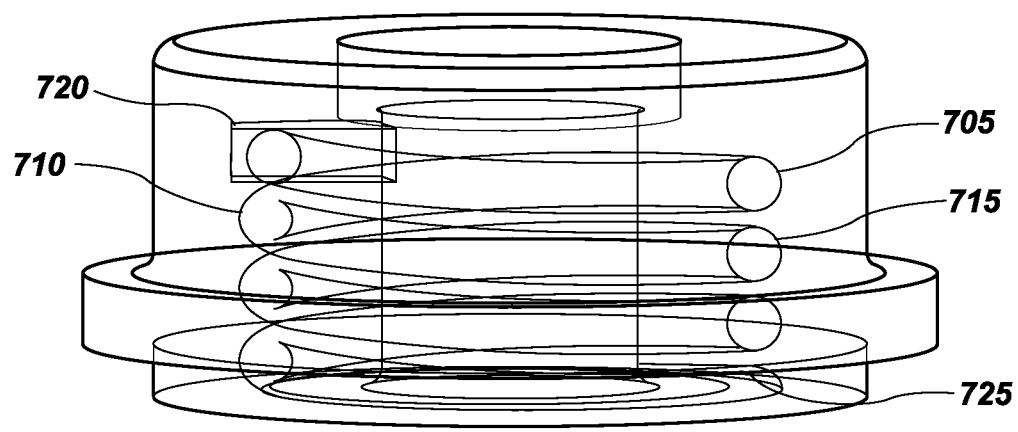
FIG. 7D illustrates an alternative embodiment of a tortuous path within a fluid collection receptacle including one or more sensors.

FIG. 7D illustrates an alternative embodiment of a tortuous path 720 within a fluid collection receptacle 700 including one or more sensors in a pressure sensor component 705. Tortuous path 720 includes a spiral 710 which may be termed a spiral down embodiment. Spiral 710 may proceed downward in a plurality of rings 715 to an output 725.

Figure 8:
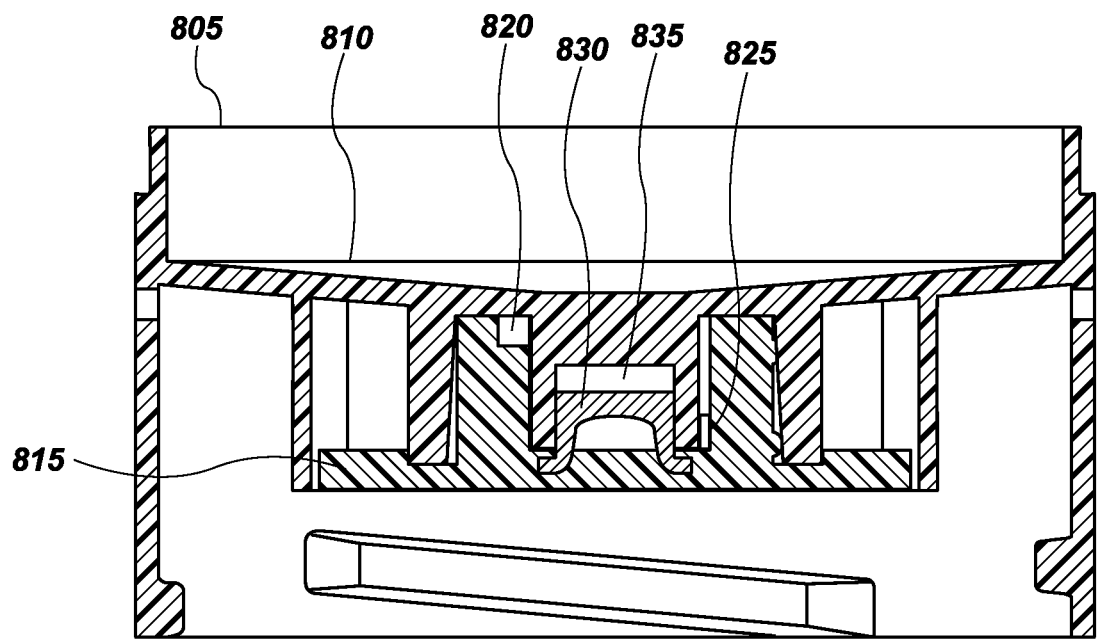
FIG. 8 illustrates an alternative embodiment of a tortuous path within a fluid collection receptacle including one or more sensors.

FIG. 8 illustrates an alternative embodiment of a tortuous path 820 within a fluid collection receptacle 800 including one or more sensors. Fluid collection receptacle 800 may be similar to other fluid collection receptacles and bottles disclosed herein. As shown in FIG. 8, a fluid collection receptacle 800 includes a bottle 805. Bottle 805 includes a bottom 810 which slopes downwardly in a funnel-like manner, to an entrance to tortuous path 820. Tortuous path 820 is created by an interface between a membrane 815 and bottle 805 with an output 825 into an air chamber 835. A partial right angle snake 830 is installed within tortuous path 820 and within membrane 815 or is created between membrane 815 and bottle 805. Fluid collection receptacle 800 may implement the embodiment shown in FIG. 8 with sensors, batteries, processors, and with any other embodiment disclosed herein.

Figure 9:
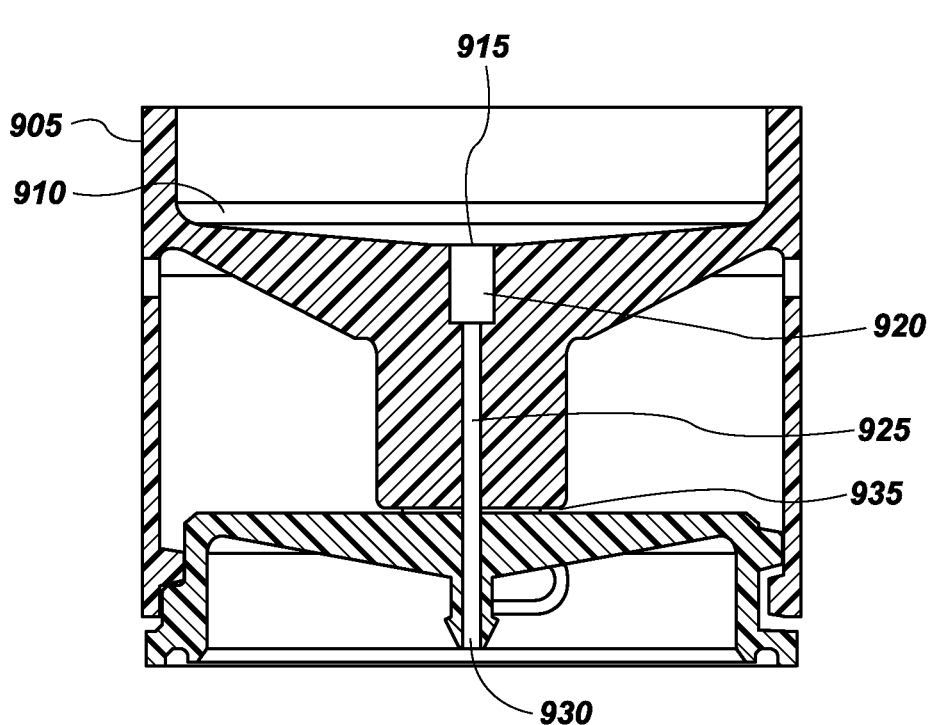
FIG. 9 illustrates an alternative embodiment of a tortuous path within a fluid collection receptacle including one or more sensors, which includes an initial pressure-controlling chamber.

FIG. 9 illustrates an alternative embodiment of a tortuous path 925 within a fluid collection receptacle 900 including one or more sensors which includes an initial pressure-controlling chamber. As shown in FIG. 9, fluid collection receptacle 900 includes a bottle 905. Bottle 905 has a bottom that is formed with a downward slope, like a funnel, to cause fluid within bottle 905 to flow towards hole 915. Hole 915 may be open and not include a membrane in this embodiment. Hole 915 opens to a supercharger 920 which has a larger inner diameter than tortuous path 925 which connects to supercharger 920. Supercharger 920 is an initial pressure controlling chamber that allows liquid draining into supercharger 920 to initiate the beginning of a pressure increase within tortuous path 925. Supercharger 920 may be used with direct contact systems. However, since direct contact systems are without a membrane, liquid may fall into the tortuous path 925 when bottle 905 initially fills with liquid which can cause unpredictable pressure spikes. Supercharger 920 controls an amount of liquid that contributes to the unpredictable pressure spikes to lessen this effect or, alternatively, allow a processor to detect that a fluid has started to enter bottle 905. Supercharger 920 may be implemented in a membrane element or in bottle 905.

As liquid within supercharger 920 attempts to drain into tortuous path 925, air within tortuous path 925 pushes back against the liquid, increasing pressure within tortuous path 925. Supercharger 920 and tortuous path 925 may be positioned in a straight line to a pressure sensor 930 which detects pressure increases in tortuous path 925 as more and more liquid is collected by bottle 905. An O-ring 935 may be fitted between a pressure sensor component and a bottom of bottle 905 to ensure that an air-tight seal is formed between bottle 905 and a pressure sensor component. O-ring 935 may also be implemented as a co-molded gasket that is implemented on the pressure sensor component.

Figure 10:
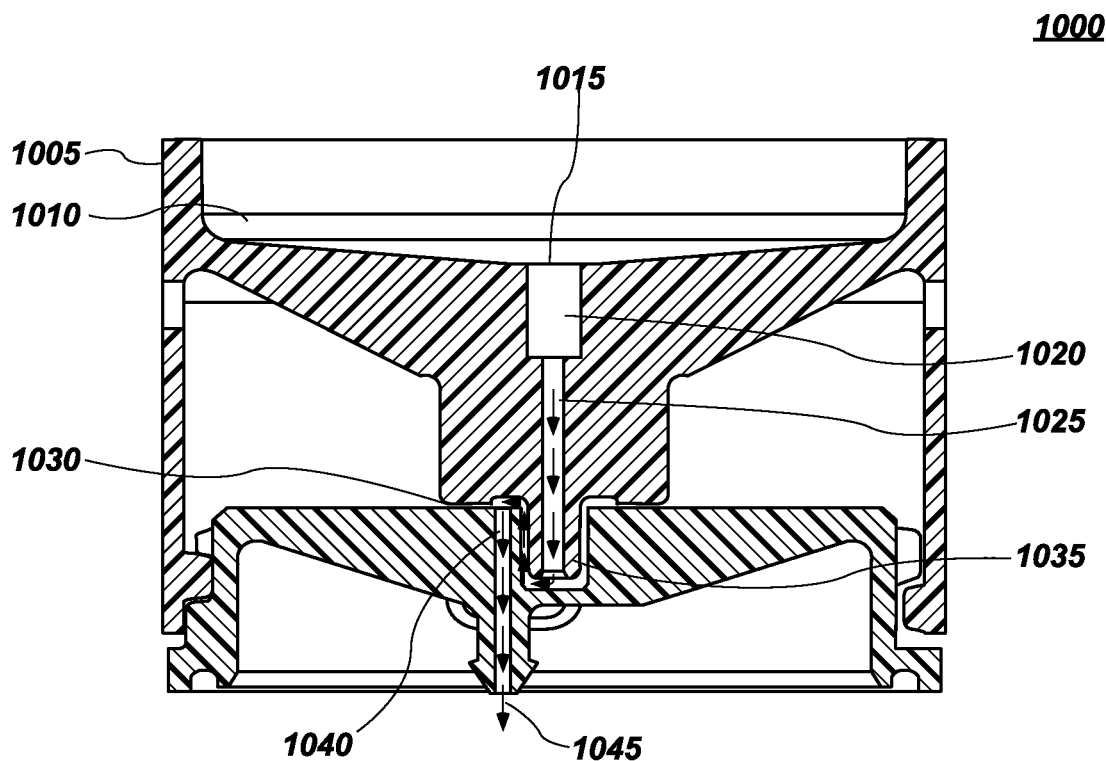
FIG. 10 illustrates an alternative embodiment of a tortuous path within a fluid collection receptacle including one or more sensors.

FIG. 10 illustrates an alternative embodiment of a tortuous path 1025 within a fluid collection receptacle 1000 including one or more sensors. As shown in FIG. 10, fluid collection receptacle 1000 includes a bottle 1005. Bottle 1005 has a bottom that is formed with a downward slope, like a funnel, to cause fluid within bottle 1005 to flow towards hole 1015. Hole 1015 may be open and not include a membrane in this embodiment. Hole 1015 opens to a supercharger 1020 which has a larger inner diameter than tortuous path 1025 which connects to supercharger 1020. Supercharger 1020 is an initial pressure controlling chamber that allows liquid draining into supercharger 1020 to initiate the beginning of a steep pressure increase within tortuous path 1025. As liquid within supercharger 1020 attempts to drain into tortuous path 1025, air within tortuous path 1025 pushes back against the liquid, increasing pressure within tortuous path 1025. As shown in FIG. 10, a plurality of arrows illustrate the flow and direction of flow of air and/or liquid in the tortuous path, as will be described below. Supercharger 1020 and tortuous path 1025 may be include an upward bend 1035 which forces liquid that may drain into tortuous path 1025 to go up, against gravity and against pressure created within fluid collection receptacle 1000. In this embodiment, tortuous path 1025 may include another bend at O-ring 1030 which may drain into a straight portion downward portion 1040 of tortuous path 1025 and into pressure sensor 1045. Arrows associated with tortuous path 1025 show an intended direction of flow relative to fluid collection receptacle 1000. Because any liquid within bottle 1005 is forced to fight gravity and pressure, it is less likely that liquid can get to the sensor.

An O-ring 1030 may be fitted between a pressure sensor component and a bottom of bottle 1005 to ensure that an air-tight seal is formed between bottle 1005 and a pressure sensor component. O-ring 1035 may also be implemented as a co-molded gasket that is implemented on the pressure sensor component.

Figure 11:
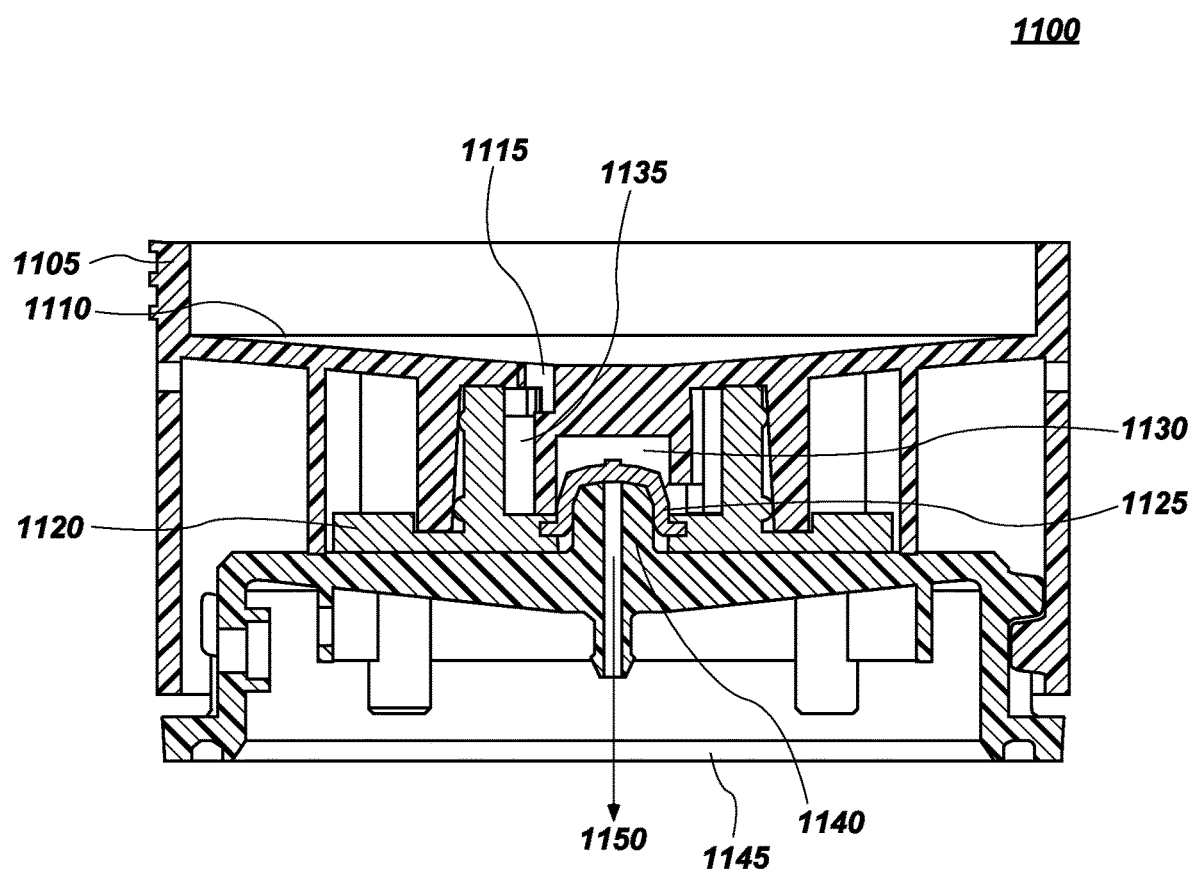
FIG. 11 illustrates an alternative embodiment of a fluid collection receptacle implementing an access valve and a tortuous path and including one or more sensors.

FIG. 11 illustrates an alternative embodiment of a fluid collection receptacle 1100 implementing an access valve 1125 and a tortuous path 1135 and including one or more sensors. As shown in FIG. 11, fluid collection receptacle 1100 includes a bottle 1105. Bottle 1105 has a bottom that is formed with a downward slope, like a funnel, to cause fluid within bottle 1105 to flow towards hole 1115. Hole 1115 may be open to a tortuous path 1135 installed within a membrane element 1120. Tortuous path 1135 may be a right angle snake path and outlet into air chamber 1130 where access valve 1125 provides an opening for air and liquid to selectively pass through air chamber 1130 into a second tortuous path 1150 which provides access to a pressure sensor within a sensor element, a top of which is illustrated as element 1145. Access valve 1125 may be selectively opened and closed by a mechanical activator 1140, which will be discussed in more detail below.

As shown in FIG. 11, as liquid fills bottle 1105, liquid flows through tortuous path 1135 and into air chamber 1130. When access valve 1125 is activated by mechanical activator 1140, a pressure sensor at the end of second tortuous path 1150 may detect an amount of pressure within bottle 905 and convey that information to a processor which calculates a volume of fluid within bottle 905.

Figure 12A:
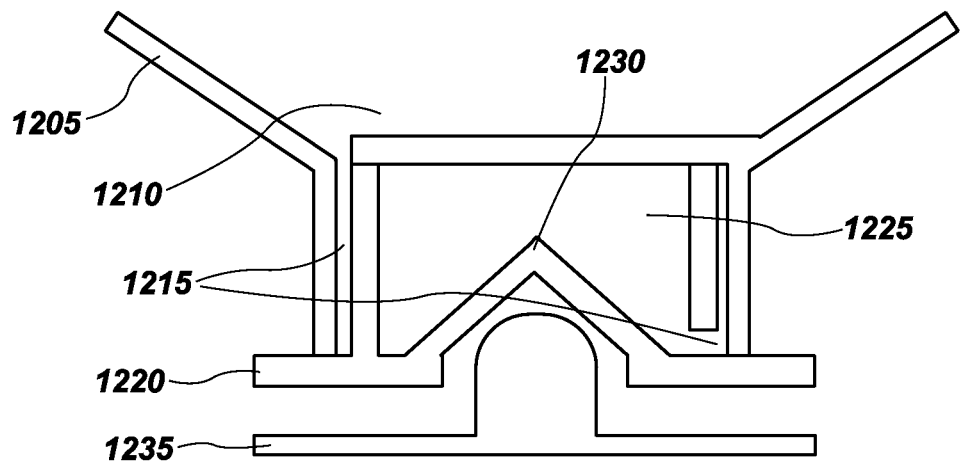
FIG. 12A illustrates an access valve associated with the fluid collection receptacle including one or more sensors in a closed configuration.

FIG. 12A illustrates an access valve 1220 associated with a fluid collection receptacle 1200 including one or more sensors in a closed configuration. Access valve 1220 corresponds to access valve 1125, discussed above with respect to FIG. 11, but in additional detail. As previously discussed with respect to FIG. 11, fluid collection receptacle 1200 includes a bottle 1205 which includes a bottom 1210 which slopes downwardly, like a funnel to provide access to a hole and tortuous path 1215. Tortuous path 1215 may be any tortuous path disclosed herein or similar implementation. Tortuous path 1215 outlets at air chamber 1225 within which is disposed access valve 1220. Access valve 1220 is implemented as part of the membrane as shown in FIG. 12A but may be otherwise implemented with an opening 1230 which selectively allows air and liquid to flow through valve 1220 depending on whether or not opening 1230 is opened or closed. Mechanical activator 1235 may be used to selectively open or close opening 1230 of valve 1220, as will be discussed below. However, in FIG. 12A, opening 1230 is closed.

Figure 12B:
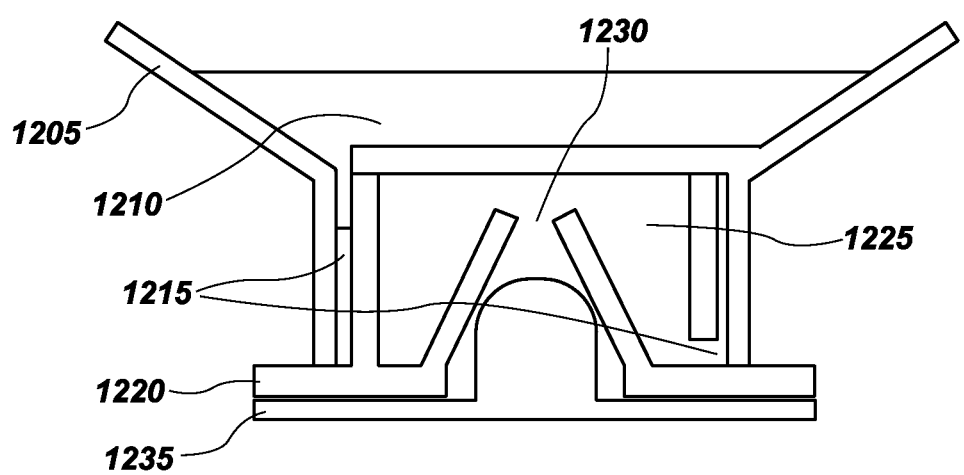
FIG. 12B illustrates an access valve associated with the fluid collection receptacle including one or more sensors in an open configuration.

FIG. 12B illustrates an access valve 1220 in an open position and associated with a fluid collection receptacle 1200 including one or more sensors. Access valve 1220 corresponds to access valve 1125, discussed above with respect to FIG. 11, and access valve 1220 discussed above with respect to FIG. 12A. As previously discussed with respect to FIG. 11, fluid collection receptacle 1200 includes a bottle 1205 which includes a bottom 1210 which slopes downwardly, like a funnel to provide access to a hole and tortuous path 1215. As shown in FIG. 12B, bottom 1210 does not include liquid. Valve 1220 may be opened prior to liquid being disposed within bottle 1205. Tortuous path 1215 may be any tortuous path disclosed herein or similar implementation. Tortuous path 1215 outlets at air chamber 1225 within which is disposed access valve 1220. Access valve 1220 is implemented with an opening 1230 which selectively allows air to flow through valve 1220 depending on whether or not opening 1230 is opened or closed. Mechanical activator 1235 may be used to selectively open or close opening 1230 of valve 1220, as will be discussed below. In FIG. 12B, mechanical activator 1235 has opened opening 1230 in valve 1220 by forcing mechanical activator 1235 into valve 1220 such that valve 1230 is forced open. As opening 1230 is opened, an air path is created to a pressure sensor which can detect changes in pressure within bottle 1205.

Figure 12C:
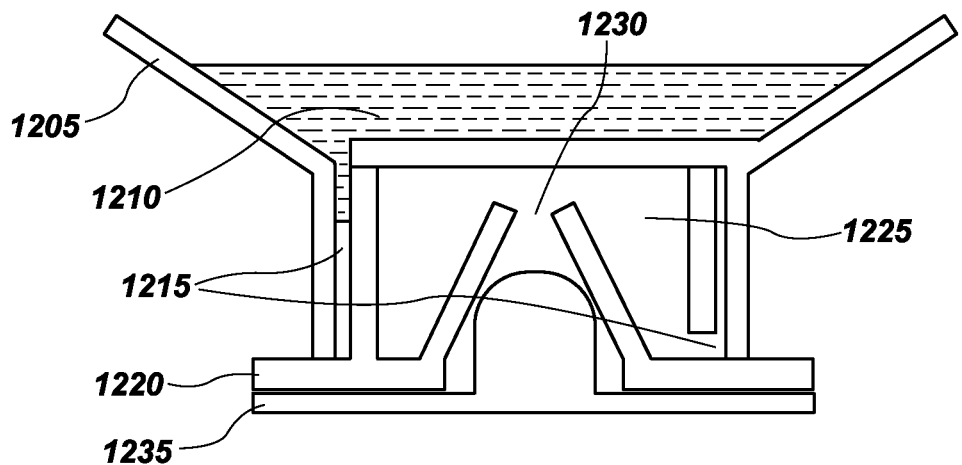
FIG. 12C illustrates an access valve associated with the fluid collection receptacle including one or more sensors in an open configuration when the receptacle contains a liquid.

FIG. 12C illustrates an access valve 1220 associated with the fluid collection receptacle 1200 including one or more sensors in an open configuration when fluid collection receptacle 1200 contains a liquid. Access valve 1220 corresponds to access valve 1125, discussed above with respect to FIG. 11, and access valve 1220 discussed above with respect to FIGS. 12A and 12B. As previously discussed with respect to FIG. 11, fluid collection receptacle 1200 includes a bottle 1205 which includes a bottom 1210 which slopes downwardly, like a funnel to provide access to a hole and tortuous path 1215. As shown in FIG. 12C, bottom 1210 includes liquid. Tortuous path 1215 may be any tortuous path disclosed herein or similar implementation. Tortuous path 1215 outlets at air chamber 1225 within which is disposed access valve 1220. Access valve 1220 is implemented with an opening 1230 which selectively allows air to flow through valve 1220 depending on whether or not opening 1230 is opened or closed. Mechanical activator 1235 may be used to selectively open or close opening 1230 of valve 1220. In FIG. 12C, mechanical activator 1235 has opened opening 1230 in valve 1220 by forcing mechanical activator 1235 into valve 1220 such that valve 1230 is forced open. As opening 1230 is opened, an air path is created to a pressure sensor which can detect changes in pressure within bottle 1205.

Figure 12D:
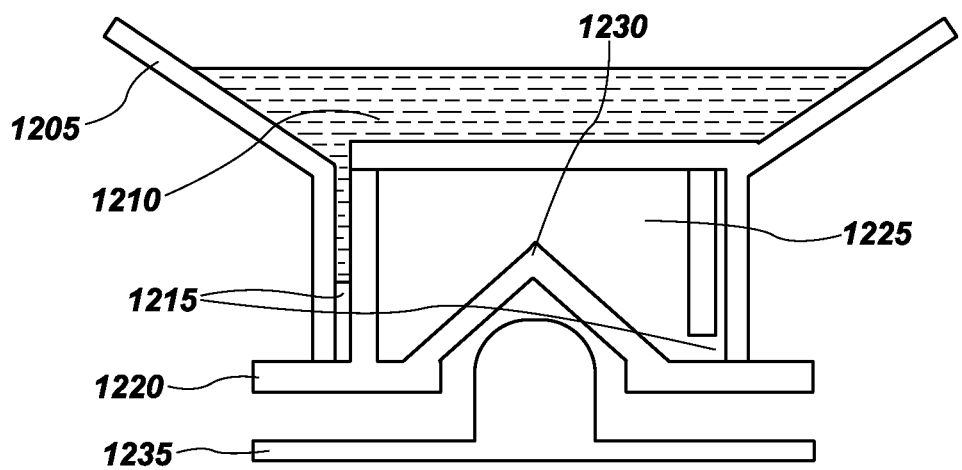
FIG. 12D illustrates an access valve associated with the fluid collection receptacle including one or more sensors in a closed configuration when the receptacle contains a liquid.

FIG. 12D illustrates an access valve 1220 associated with the fluid collection receptacle 1200 including one or more sensors in a closed when fluid collection receptacle 1200 contains a liquid. Access valve 1220 corresponds to access valve 1125, discussed above with respect to FIG. 11, and access valve 1220 discussed above with respect to FIGS. 12A, 12B, and 12C. As previously discussed with respect to FIG. 11, fluid collection receptacle 1200 includes a bottle 1205 which includes a bottom 1210 which slopes downwardly, like a funnel to provide access to a hole and tortuous path 1215. As shown in FIG. 12C, bottom 1210 includes liquid. Tortuous path 1215 may be any tortuous path disclosed herein or similar implementation. Tortuous path 1215 outlets at air chamber 1225 within which is disposed access valve 1220. Access valve 1220 is implemented with an opening 1230 which selectively allows air to flow through valve 1220 depending on whether or not opening 1230 is opened or closed. Mechanical activator 1235 may be used to selectively open or close opening 1230 of valve 1220. In FIG. 12D, mechanical activator 1235 has closed opening 1230 in valve 1220 by removing mechanical activator 1235 from valve 1220 such that valve 1230 returns to a biased closed position. In this manner air chamber 1225 is maintained, preventing liquid from entering air chamber 1225 by air pressure but liquid is not allowed to reach the valve.

Figure 13A:
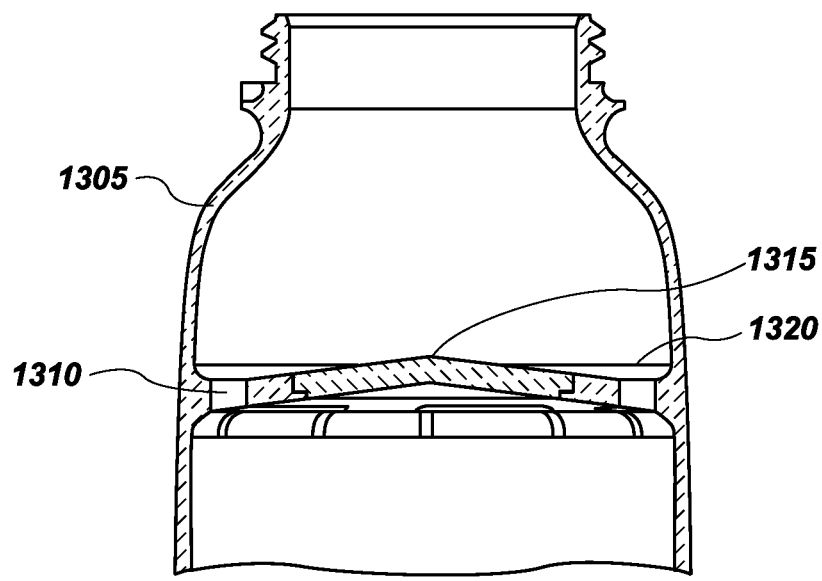
FIG. 13A illustrates a fluid collection receptacle including a diffuser.

FIG. 13A illustrates a fluid collection receptacle 1300 including a diffuser 1315. Fluid collection receptacle 1300 includes a bottle 1305. Diffuser 1315 is disposed within the bottle and includes an outer edge 1310 within which are a plurality of holes 1320. A center portion of diffuser 1315 may be raised to provide a slope, which allows liquid dropping into bottle to be diffused to the outside edge 1310 of the diffuser and pass through one of the plurality of holes 1320 into a lower portion of bottle 1305. Diffuser 1315 acts as a passive filter to stabilize pressure readings as measured by the sensing component below the liquid receptacle, not shown.

Figure 13B:
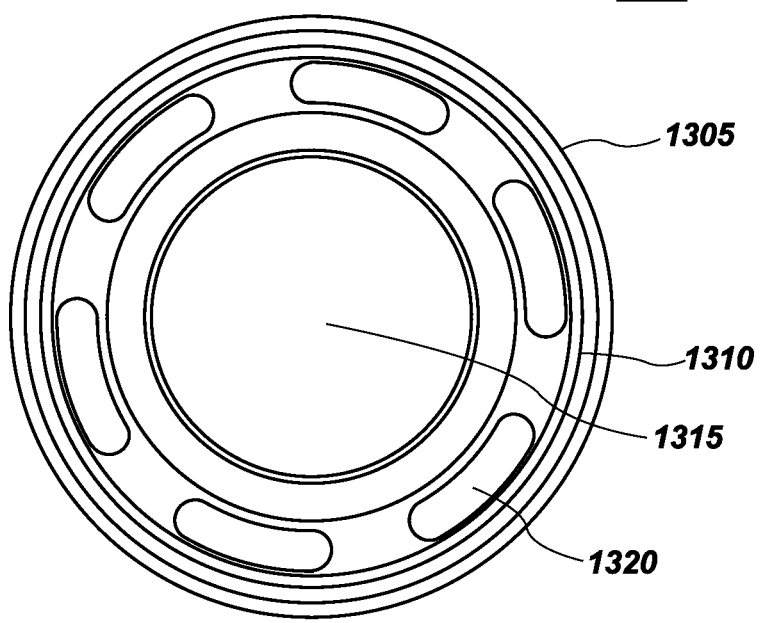
FIG. 13B illustrates a top view of the diffuser.

FIG. 13B illustrates a top view of diffuser 1300. As shown in FIG. 13A, diffuser 1300 is disposed in a bottle 1305 and includes an outer edge 1310. A center portion 1315 of diffuser 1300 is raised to provide a slope for liquid dropping into the bottle to be diffused to the outside edge 1310 and pass through one of the plurality of holes 1320 into a lower portion of bottle 1305.

Figure 14A:
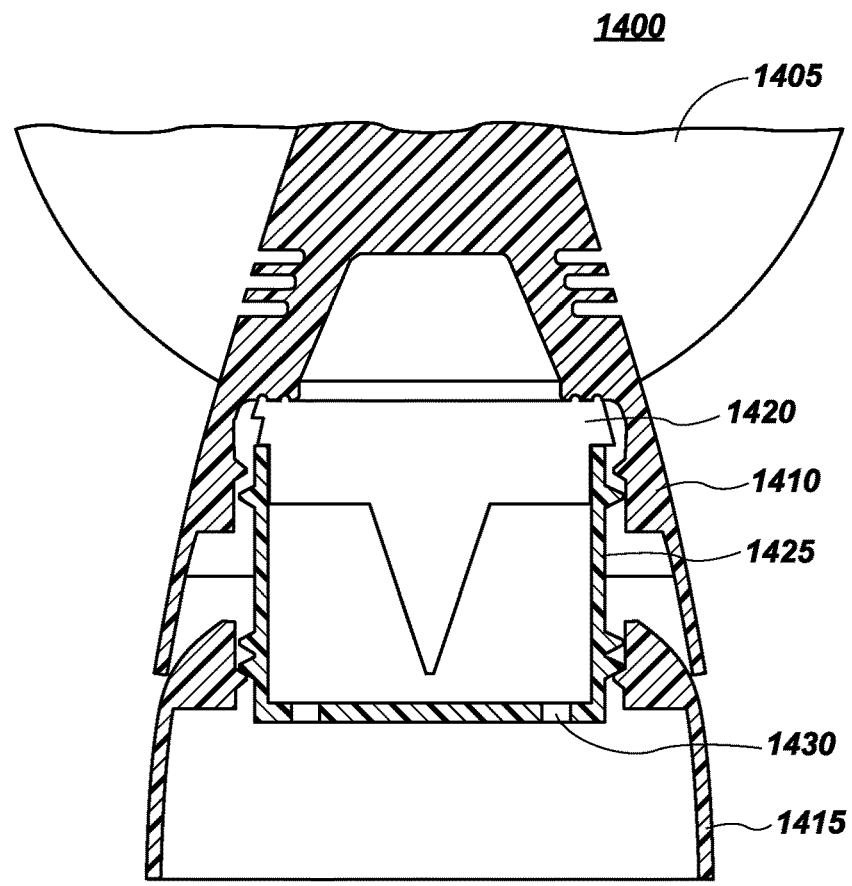
FIG. 14A illustrates a cross sectional view of a breast pump including fluid collection receptacle with a removable diffuser.

FIG. 14A illustrates a cross sectional view of a breast pump 1400 including fluid collection receptacle 1415 with a removable diffuser 1425. Breast pump 1400 may include a flange 1405, a manifold 1410, and a fluid collection receptacle 1415. As shown in FIG. 14A, a diffuser 1425 is implemented with a valve 1420. Valve 1430 rests on a top portion of diffuser 1420 and may be connected as a friction fitting. Valve 1425 may allow liquid to pass through valve 1425 as vacuum pressure on breast pump 1400 cycles. Once liquid passes through valve 1425, diffuser 1425 is implemented with a plurality of holes 1430 which diffuse the liquid as it passes through into fluid collection receptacle 1415. Diffuser 1425 dampens a flow of liquid as it leaves valve 1425 and allows liquid to move less turbulently into fluid collection receptacle 1415. By diffusing liquid as it falls into fluid collection receptacle 1415, a supercharger may be filled with liquid before filling fluid collection receptacle 1415 which can help limit liquid entering an air chamber and uncontrollable pressure spikes, as discussed above.

Figure 14B:
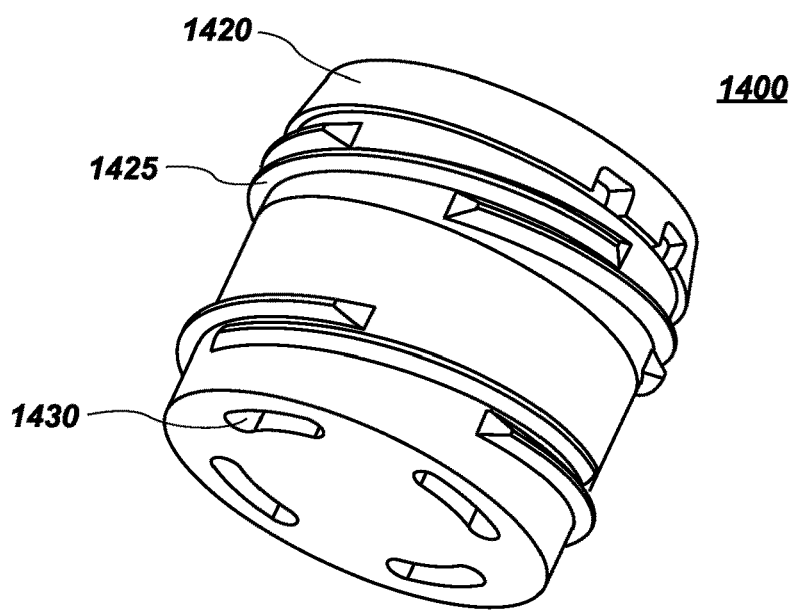
FIG. 14B illustrates a perspective view of the removable diffuser with installed valve.

FIG. 14B illustrates a perspective view of the removable diffuser 1425 with installed valve. Diffuser 1425 may be threaded to engage with manifold 1410, shown in FIG. 14A on a top end and threaded to engage with fluid collection receptacle 1415, shown in FIG. 14A on a bottom end. Valve 1420 is installed on diffuser 1420 which selectively allows milk to fall into diffuser 1420 and through a plurality of holes 1430. As shown in FIG. 14B, a plurality of holes 1430 are disposed in diffuser 1425. However, a single hole may also be implemented depending on implementation. Further, holes 1430 may be disposed anywhere in the bottom of diffuser 1425, including the center, and may radiate from inside to outside (or center to outside edge).

Figure 15:
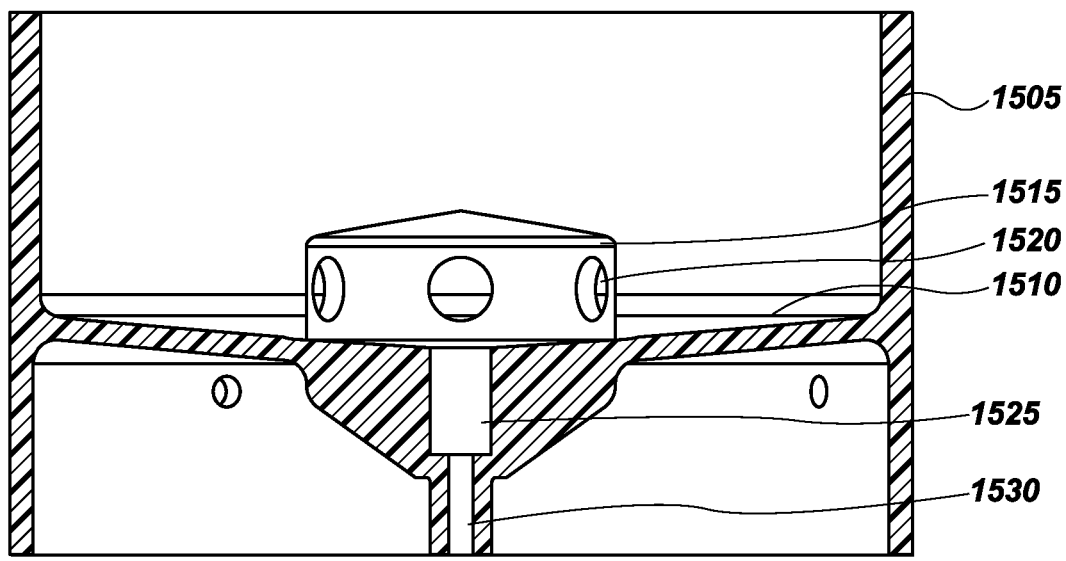
FIG. 15 illustrates fluid collection receptacle having a diffuser at a bottom of the fluid collection receptacle.

FIG. 15 illustrates fluid collection receptacle 1500 having a diffuser 1515 at a bottom 1510 of the fluid collection receptacle 1500. As previously discussed, fluid collection receptacle 1500 may include a bottle 1505 that includes a bottom 1510 which is sloped downwardly, like a funnel, to allow liquid to slope towards a center of bottle 1505. At this point, diffuser 1515 may receive liquid through one or more of a plurality of slots 1520 disposed within an outside surface of diffuser 1515. The plurality of slots 1520 may be circular or may be oval, rectangular, square, or any other shape and allow liquid to pass from an outside surface of diffuser 1515 to an inside of the diffuser 1515. Diffuser 1515 may be connected to a supercharger 1525 which is connected to a tortuous path 1530 using techniques described above to create pressure to be detected by pressure sensor 1535, not shown.

Diffuser 1515 may be disposed at the bottom of bottle 1505 and closer to the air chamber above pressure sensor 1535. Diffuser 1515 may be integrated into the bottle or may be a separate individual removable element to facilitate cleaning. Diffuser 1515 implemented as a separate individual removable element increases the modularity of the bottle size and base components.

The foregoing description has been presented for purposes of illustration. It is not exhaustive and does not limit the invention to the precise forms or embodiments disclosed. Modifications and adaptations will be apparent to those skilled in the art from consideration of the specification and practice of the disclosed embodiments. For example, components described herein may be removed and other components added without departing from the scope or spirit of the embodiments disclosed herein or the appended claims.

Other embodiments will be apparent to those skilled in the art from consideration of the specification and practice of the disclosure disclosed herein. It is intended that the specification and examples be considered as exemplary only, with a true scope and spirit of the invention being indicated by the following claims.

What is claimed is:

1. A liquid receptacle, comprising
a bottle having a top and a bottom, the bottom including a hole which extends through the bottom of the bottle; and
a pressure sensor element disposed in the bottom of the bottle, the pressure sensor element including a membrane that includes a valve and seals the hole which extends through the bottom of the bottle.

2. The liquid receptacle of claim 1, wherein an inside of the bottom of the bottle includes threads.

3. The liquid receptacle of claim 2, wherein an outside of the pressure sensor element includes threads corresponding to the threads in the inside of the bottom of the bottle.

4. The liquid receptacle of claim 1, wherein the pressure sensor element is a base for the bottle.

5. The liquid receptacle of claim 1, wherein a pressure sensor is disposed below the membrane and within the pressure sensor element.

6. The liquid receptacle of claim 1, wherein a path is disposed below the membrane and a pressure sensor is disposed at an end of the tortuous path within the pressure sensor element.

7. The liquid receptacle of claim 1, wherein the membrane is removable from the pressure sensor element.

8. The liquid receptacle of claim 1, wherein the membrane includes a hole leading to a path disposed below the membrane.

9. The liquid receptacle of claim 1, wherein the membrane includes one or more gaskets disposed on a surface of the membrane.

10. The liquid receptacle of claim 1, wherein the pressure sensor element includes a pressure sensor.

11. The liquid receptacle of claim 1, wherein the pressure sensor element includes an accelerometer.

12. The liquid receptacle of claim 1, wherein the pressure sensor element includes a temperature sensor.

13. The liquid receptacle of claim 1, wherein the pressure sensor element includes a processor.

14. The liquid receptacle of claim 13, wherein the processor is configured to receive information from a pressure sensor and determined, based on the information received from the pressure sensor, a volume of liquid in the bottle.

15. The liquid receptacle of claim 13, wherein the processor is configured to receive information from a pressure sensor and determine, based on information received from the pressure sensor, a flow rate of fluid entering the bottle.

16. The liquid receptacle of claim 1, wherein the pressure senor element includes a battery.

17. A system, comprising:
a flange;
a manifold connectable to the flange and including a connector;
a liquid receptacle connectable to the manifold by the connector and including a hole which extends through a bottom of the liquid receptacle; and
a pressure sensor element disposed in the bottom of the liquid receptacle, the pressure sensor element including a membrane that includes a valve and seals the hole which extends through the bottom of the liquid receptacle.

18. The system of claim 17, wherein the membrane provides one of a direct contact system or a closed system.

* * * * *